Figure 1:
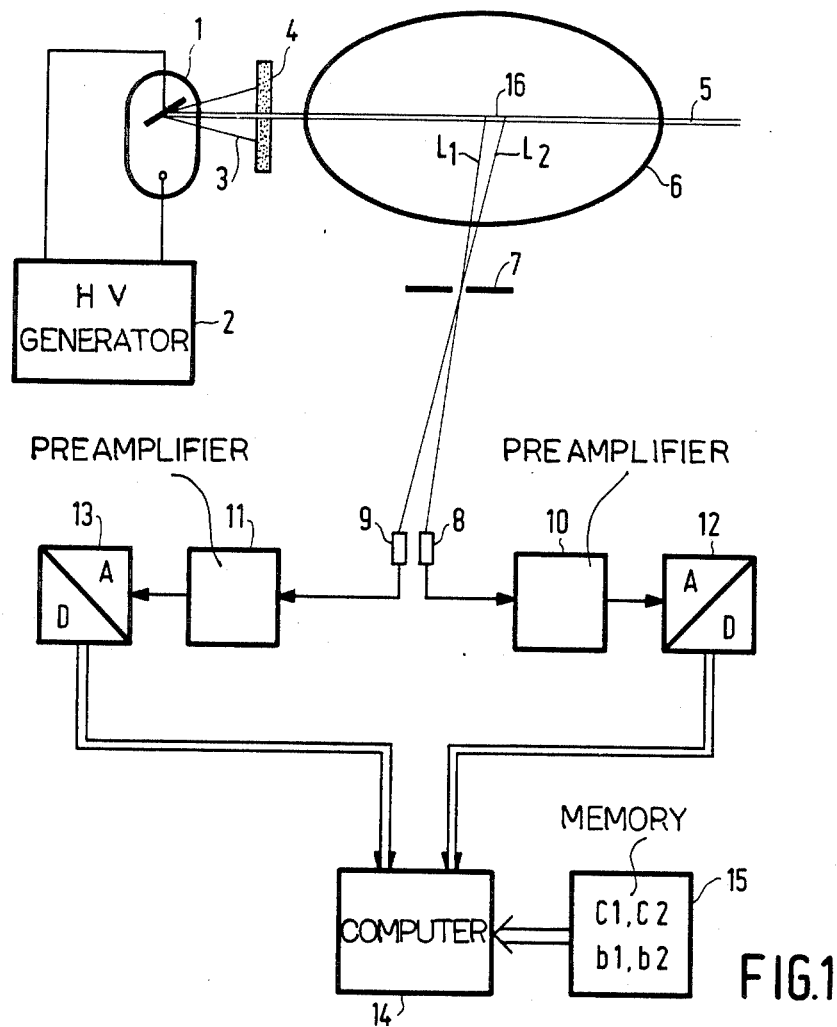

United States Patent [19]

Harding et al.

[11] Patent Number: 4,785,401
[45] Date of Patent: Nov. 15, 1988

[54] METHOD AND DEVICE FOR DETERMINING AN ENERGY-INDEPENDENT X-RAY ATTENUATION FACTOR IN A REGION OF AN OBJECT

[75] Inventors: Geoffrey Harding, Halstenbeck; Josef-Maria Kosanetzky, Norderstedt, both of Fed. Rep. of Germany

[73] Assignee: U.S. Philips Corporation, New York, N.Y.

[21] Appl. No.: 909,807

[22] Filed: Sep. 22, 1986

[30] Foreign Application Priority Data

Sep. 28, 1985 [DE] Fed. Rep. of Germany ....... 3534702

[51] Int. Cl.⁴ .......................................... G01N 23/201
[52] U.S. Cl. .................................. 364/413.16; 378/88
[58] Field of Search .................... 364/414; 378/88, 86

[56] References Cited

U.S. PATENT DOCUMENTS

| | | | |
|---|---|---|---|
| 3,843,881 | 10/1974 | Barton et al. | 378/88 X |
| 3,961,186 | 6/1976 | Leunbach | 378/5 |
| 4,371,976 | 2/1983 | Wagner | 378/16 |
| 4,375,695 | 2/1983 | Harding | 378/6 |

Primary Examiner—Jerry Smith
Assistant Examiner—Steven G. Kibby
Attorney, Agent, or Firm—Jack E. Haken

[57] ABSTRACT

A method and apparatus for measurement of an energy-independent attenuation factor in a predetermined area of a primary X-ray beam which passes through a test object. Two detectors measure scattered radiation on closely adjacent paths in each of two different spectral ranges. The attenuation factor is calculated from the difference of the logarithms of quotients of measurements taken at different energies.

5 Claims, 2 Drawing Sheets

METHOD AND DEVICE FOR DETERMINING AN ENERGY-INDEPENDENT X-RAY ATTENUATION FACTOR IN A REGION OF AN OBJECT

The invention relates to a method and device for determining an energy-independent X-ray attenuation factor in an area of a test object traversed by a primary beam. Scattered radiation generated in the primary beam is measured and the attenuation factor is determined from the measured values. Herein, the attenuation factor $A_p$ is defined as an energy-independent quantity which characterizes X-ray interactions with material within a region in the test object.

BACKGROUND OF THE INVENTION

Such a method, which can be applied in principle in medical diagnostics or in materials testing (including the testing of food-stuffs), is known from J. Phys. E: Sci. Instrum., Vol. 18, 1985, pages 354 to 357. With this method, designated the "ratio method", the test object is traversed by a primary beam and the scattered radiation generated in the test object in the relevant area of the primary beam and leaving the test object at an angle of 90° is measured and in fact divided into a Compton component and an elastic scattered-radiation component. From the ratio of the elastic scattered-ratiation component to the Compton component it is possible to deduce the attenuation factor in the said area of the primary beam.

The separate determination of Compton scattered radiation and elastic scattered radiation utilizes the fact that in a Compton scattering process the energy of an X-ray quantum decreases whilst in elastic scattering (so-called Rayleigh scattering) the scattered X-ray quantum does not undergo any change of energy. To enable Compton scattered radiation and elastic scattered radiation to be distinguished from one another, the amplitude of the pulses generated by the arrival of the X-ray quanta, which is proportional to the energy of the X-ray quanta, has to be determined and evaluated by means of a pulse-height analyser and to make that in fact possible, monochromatic X-radiation has to be used. Radiation sources for monochromatic X-radiation, however, are of essentially lower intensity than radiation sources for polychromatic X-radiation. Additionally, the scattering angle which the scattered radiation detected during measurement makes with the primary beam has to be relatively large—e.g. 90°—so that the energy difference between the elastic scattered radiation and the Compton radiation can be evaluated. With such large scattering angles, however, the intensity of the elastically scattered radiation is very low, while elastically scattered radiation is concentric in the forward direction if the radiation energy is sufficiently high (60 keV) in order to penetrate typical objects. For the reasons stated extremely long measuring times are required in order to achieve sufficiently accurate results.

SUMMARY OF THE INVENTION

An object of the invention is to provide a method for measuring the attenuation factor which does not require a separate measurement of elastically scattered radiation components. This problem is solved by using two detector configuration to measure the scattered radiation from two non-identical sections of the primary beam in two different spectral ranges and determining the attenuation factor from the measured values thus obtained using the relation:

$$A_p = |d1^*(\ln Q1 - b1) - d2^*(\ln Q2 - b2)| \qquad (1)$$

where d1, d2, b1 and b2 are constants and Q1 if the quotient of the measured values from the first detector configurations of the first and second spectral ranges and Q2 the quotient of the measured values from the second detector configuration for the first and second spectral ranges.

The invention is based on the following consideration. The intensity of the scattered radiation determined by one of the two detector configurations depends not only the electron density and the scatter cross-section area in the section of the primary beam whose scattered radiation is being determined by the particular detector configuration, but also on the total attenuation which the X-radiation undergoes on its path from entry into the object to the relevant section and from the latter (as scattered radiation) to the detector configuration. This total attenuation of the X-radiation is caused on the one hand by its scattering and on the other hand by its absorption, i.e. the attenuation of the radiation consists of a scatter component and an absorption component. The scatter component is essentially independent of the energy of the X-radiation or of the energy spectral range, while the absorption component, produced primarily by photoelectric absorption, depends closely on the energy (it is inversely proportional to the third power of the energy). The scatter component of the total attenuation is thus equally great in the different spectral ranges measured by a detector configuration. For that reason and because of an exponential relationship between the intensity of the scattered radiation and the attenuation, the scatter component is eliminated if the logarithm of the two measured values is taken. This quotient therefore depends essentially only on the photoelectric absorption along the path which the primary radiation or the scattered beam has taken through the object.

The same applies to the logarithm of the quotient of the two measured values from the other detector configuration. Since the scattered rays cover practically the same path through the object with a suitable position of the detector configurations, the two quotients differ only in the area of the primary beam located between the two sections whose scattered radiation is being determined by the detector configurations. The difference between the two said logarithms is therefore a measure of the attenuation factor in this area.

The arrangement for implementation of the method has an X-ray tube for the generation of an X-ray beam, a first diaphragm arrangement for the stopping-down of a primary beam, two detector configurations which detect the scattered radiation from two sections of the primary beam by means of a second diaphragm arrangement and which are so arranged that they are reached by the X-radiation via practically the same paths, and a computing device for determining the attenuation factor from the measured values.

There are various possibilities for measuring in two spectral ranges. One possibility consists in performing two measurements one after the other with different spectra of the primary beam. In a further version, this can also be done by connecting the X-ray tube to a high voltage generator whose voltage can be changed over. It is well known that the bremsstrahlung spectrum which is generated in an X-ray tube depends on the voltage at the X-ray tube. The spectrum is thus changed by changing this voltage.

In the case described above the energy spectrum of the X-ray tube itself is changed between the two measurements. It is, however, also possible to leave this energy spectrum unchanged and to fit in front of the test area a changeover filter which affects the X-radiation in the two switched positions of the filter differently so that two different energy spectra are obtained. In this case, however, both spectral ranges have the same upper energy limit which is defined by the tube voltage. The spectra therefore do not differ so markedly from each other as with the previously described arrangement.

A further possibility of obtaining measured scattered radiation values in two different spectral ranges consists, according to a further development of the invention, in having each detector configuration contain a detector which converts the scattered radiation in two different spectral ranges each into an electrical signal. In this process, therefore, the energy spectrum in the primary beam is left completely unchanged but the detector—a so-called split detector—delivers two electrical signals which correspond to the intensity of the stray radiation in two different spectral ranges. Compared with the first-mentioned version, this has the advantage that only one measurement is effected but also the disadvantage that for each of the two signals which a detector configuration delivers there has to be a processing channel (pre-amplifier, etc.).

The invention does not demand the use of a monochromatic radiation source for generation of the primary beam. It is therefore possible to use an X-ray tube which provides a bremsstrahlung spectrum with a very high intensity, so that short measuring times result. A shortening of the measuring time also results from the fact that the energy of the X-ray quanta need not be measured and that the elastically scattered radiation need not be determined separately.

THE DRAWINGS

Figure 2:
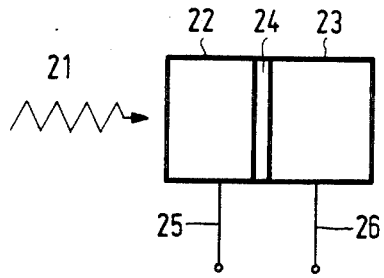
Figure 2A:
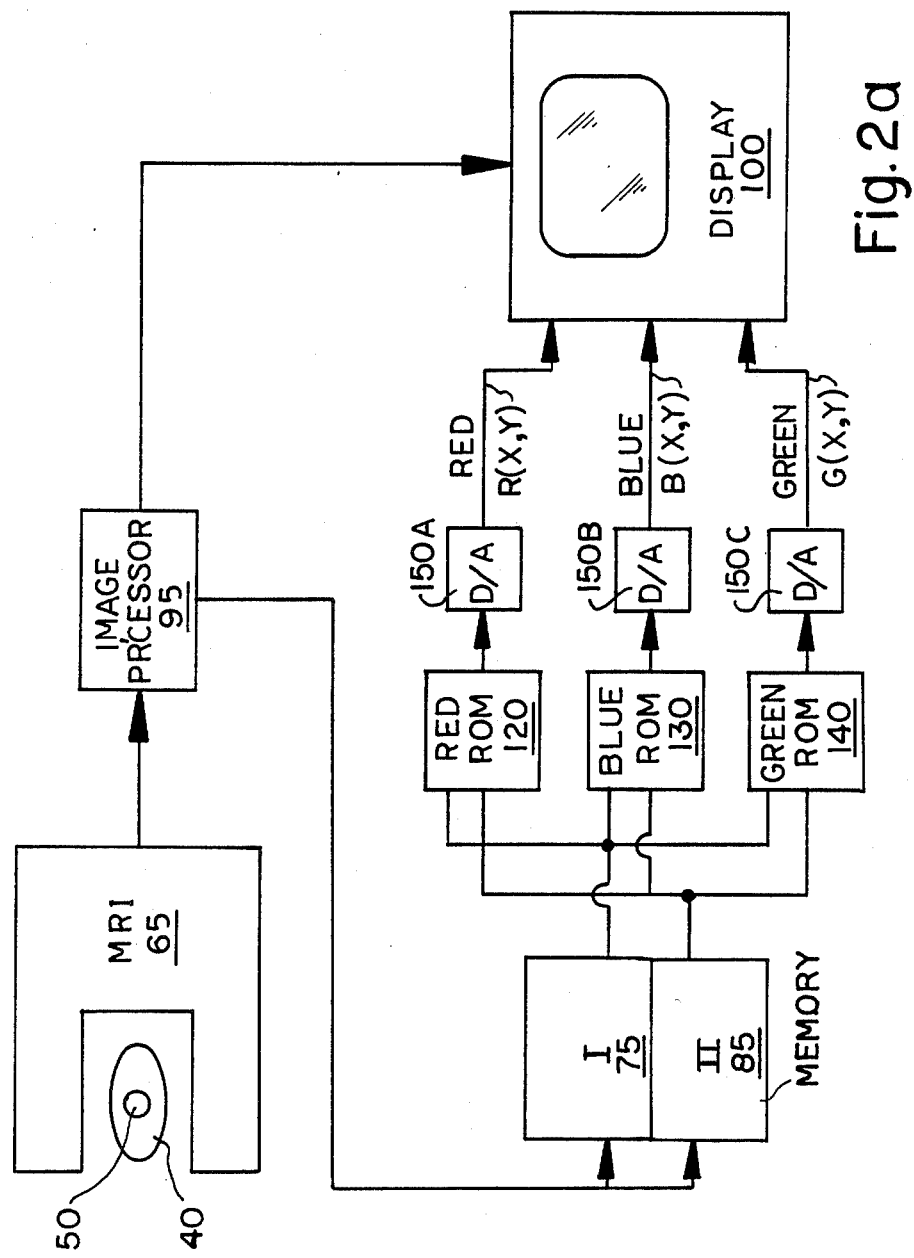

The invention will now be further explained with reference to the drawing:

FIG. 1 shows a schematic diagram of an example of embodiment of the invention, and FIG. 2 shows a special form of embodiment of a detector configuration.

EMBODIMENTS OF THE INVENTION

In FIG. 1 item 1 is an X-ray tube is connected to a high voltage generator 2 which can be switched to two different high voltages, e.g. 100 kV and 160 kV. From the X-ray beam 3 emitted by the X-ray tube there is derived, with the aid of a first diaphragm configuration 4, a thin primary beam 5 (pencil beam), i.e. a beam with only a small cross-section (e.g. 2 mm×2 ( mm) perpendicular to its direction of propagation. The primary beam traverses a test object 6 and produces scattered radiation in it. A part of the scattered radiation, which leaves the test object at an angle exceeding 90° (in relation to the direction of propagation of the beam) reaches, via a second diaphragm arrangement 7 with a small aperture in the direction of propagation of the primary beam, two detectors 8 and 9 which are arranged close to one another.

Each of the two detectors 8 and 9 "sees" through the opening in the diaphragm a certain comparatively small, approximately point-like section of the primary beam, i.e. it detects the scattered radiation produced in this section of the primary beam and travelling in the direction of the connecting lines L1 and L2 to the detectors 8 and 9, respectively. The output signals from detectors 8 and 9 are taken respectively via pre-amplifiers 10 and 11 and analog-digitial converters 12 and 13 to a computing device 14. To determine the attenuation factor in the area 16 of the primary beam, which is located between the sections whose stray radiation is detected by detectors 8 and 9, a first measurement is made for a tube voltage of 100 kV and a second for a tube voltage of 160 kV. The two measured values which each of detectors 8 and 9 now provide are processed in the computing device 14 making use of the constants d1, d2, b1 and b2 stored in a memory 15. This processing is based on the following considerations.

The total attenuation which the X-radiation undergoes on its path through the test object to one of the detectors depends exponentially on the integral of a total attenuation coefficient, u, along the path covered. Accordingly, the signal S11 which detector 8 detects in the first spectral range E1 is given by the relation $$S11 = c11 * \exp\left(-\int_{L1} u(x,E1) dx\right). \quad (2)$$

In this expression c11 is a proportionality constant which relates such factors as measuring time and detector sensitivity, and u(x,E1) is a total attenuation coefficient depending on the position x and the energy E1. Correspondingly, the signal S12 which the same detector generates for the second X-ray spectrum E2 is given by $$S12 = c12 * \exp\left(-\int_{L1} u(x,E2) dx\right). \quad (3)$$

If the quotient S11/S12 is defined as Q1 and the latter is logarithmed, equations (2) and (3) yield $$\ln Q1 = \int_{L1} (u(x,E2) - u(x,E1)) dx + b1 \quad (4)$$

where $b1 = \ln(c11/c12)$

The total attenuation coefficient u can be split into an absorption coefficient and a scatter coefficient each of which can, in turn, be split into a term which is only energy-dependent and a term which is only position-dependent. The following expression thus applies:

$$u(x,E) = a_c(x) * f_c(E) + a_p(x) * f_p(E) \quad (5)$$

In this expression $a_c(x)$ is a scattering coefficient which only depends on the position x (or on the scatter density at that position) while $f_c(E)$ is a scattering coefficient describing the energy-dependence of the scattering. $a_p(x)$ is then an absorption coefficient which is energy-independent and depends only on the position while $f_p(E)$ is an energy-dependent absorption coefficient. If the two voltages at which the X-ray tube 1 are operated produce X-ray spectra which lie between 80 kV and 50 kV, the scattering is practically independent of the energy, (i.e. $f_c(E)$ is a constant). On the other hand the attenuation depends strongly on the energy; (it is, as has been explained, inversely proportional to the third power of the energy).

If $f_c(E)$ is practically a constant, then inclusion of equation (5) in equation (4) yields $$\ln Q1 = \int_{L1} a_p(x) * (f_p(E2) - f_p(E1)) dx + b1 \quad (6)$$

This can be converted to equation (7)

$$A_p(L1) = \int_{L1} a_p(x)dx = d1*[\ln Q1 - b1]$$
$$d1 = 1/f_p(E2) - f_p(E1); \quad (7)$$

$A_p(L1)$ represents the energy-independent absorption factor along the path L1.

The constants d1 and b1 can be determined in the following manner: The test object 6 is replaced with a homogeneous calibration body with defined geometry and known energy-independent absorption coefficient $a_p$, so that on the basis of the given path L1 which the scattered radiation takes through this calibration body, the absorption factor can be calculated. Then the signals S11 and S12 for two different X-ray tube tensions are measured and the quotient Q1 derived from them. Next, using a second and also homogeneous calibration body with the same geometry but with an different but also known absorption coefficient $a_p$, the measuring procedure described is repeated. If the values found in the two measurements with each of the two calibration bodies or the calculated values are substituted in equation (7), then two equations for determining the unknown d1 and b1 are obtained. The measuring procedure described is preferably repeated with other calibration bodies in order to reduce the effect of measurement inaccuracies. The values d1 and b1 thus found depend only on the spectral distribution of energy in the primary beam (i.e. on the voltage at the X-ray tube) and also on the geometry of the measuring set-up. If, therefore, the subsequent measurements for determining the attenuation factor are performed at the same tube voltages and for the same position of detectors 8 and 9 and diaphragm 7 in relation to the primary beam 5, these values will not change.

Using the same procedure it is possible to obtain for the second photo-detector 9 for the attenuation factor on the path L2. The photo-attenuation given by equation (8):

$$A_p(L2) = \int_{L2} a_p(x)dx = d2*[\ln Q2 - b2] \quad (8)$$

In this expression Q2 is the quotient of the values measured by this detector for energies E1 and E2 and d2 and b2 are constants which, however, are not necessarily identical with d1 and b1. Differences between b1 and b2 result from possible differences in the sensitivities of the detectors, and differences between d1 and d2 depend on the spectral distribution of the bremsstrahlung for E1 and E2 and are not precisely identical because of the fact that the change of energy of the X-ray quanta caused by the Compton effect leads to slightly different values for in detectors 1 and 2.

If detectors 8 and 9 and the sections through the primary beam whose scattered radiation they detect are close to each other, the paths which the stray radiation covers from the primary beam 5 through the test object 6 to detectors 8 and 9 are very closely adjacent to each other. For that reason the scattered rays undergo practically the same photoelectric absorption. The photoelectric absorption which the X-radiation undergoes on the path to the first section on the primary beam detected by detector 8, is also the same for both paths L1 and L2. The two paths L1 and L2 thus differ from each other only by the segment 16 which the primary beam 5 has to traverse in order to arrive from the section detected by detector 8 on the primary beam to the section detected by detector 9. The difference $A_p$ between the attenuation factor along path L1 and the attenuation factor along path L2 according to equations (7) and (8) thus represents the attenuation factor in the region 16 of the primary beam. Using equations (7) and (8) this attenuation can be determined with the formula:

$$A_p = |d1*[\ln Q1 - b1] - d2*[\ln Q2 - b2]| \quad (9)$$

where $A_p$ is a material constant independent of the energy. Calculation of the attenuation factor $A_p$ in segment 16 is performed in the computing device 14 on the basis of the measured values from which the quotients Q1 and Q2 are arrived at and also from the constants according to equation (9) which are stored in memory 15.

In the arrangement shown in FIG. 1 it is essential to switch over the X-ray tube voltage in order to obtain successively from each detector two measured values for different spectral ranges.

Instead of that, however, it is also possible to make do with only one measurement (for a single tube voltage) if detectors 8 and 9 are replaced by the detector configuration shown in FIG. 2. This detector configuration consists of two sections 22 and 23 which are arranged one behind the other as seen in the direction of the scattered radiation 21. It is an advantage if the two sections 22 and 23 are separated by a layer 24 which hardens the X-radiation. The section 22 first impinged upon by scattered radiation is designed so that it converts essentially only the longer-wave part of the scattered radiation spectrum into an electrical signal which appears at the detector output 25. The remaining part of the scattered-radiation spectrum, possibly further hardened by layer 24, is converted into an electrical signal by section 23 at output 26. In this way the so-called split detector shown is capable of delivering signals corresponding to the intensity of the scattered radiation in two different spectral ranges. Against the advantage that only one measurement is required when detectors of this kind are used must be set the disadvantage that instead of two channels (10, and 12 or 11 and 13) four are necessary for processing of the measured values.

We claim:

1. A method for determining an energy-independent X-ray attenuation factor, $A_p$, in a region of an object comprising the steps of:

traversing the region of the object with a primary X-ray beam;

measuring the radiation which is scattered from first and second sections of the primary beam within the region of the object in each of a first and a second energy spectral range; and calculating the attenuation factor in accordance with the relationship $$A_p = |d1*[\ln Q1 - b1] - d2*[\ln Q2 - b2]|$$

wherein d1, d2, b1, and b2, are constants, Q1 is the quotient of the measured values in the first and second energy spectral ranges respectively of scattered radiation from the first section of the primary beam and Q2 is the quotient of the measured values in the first and second energy spectral ranges respectively of scattered radiation from the second section of the primary beam.

2. The method of claim 1 further comprising the steps of:

generating the primary beam with an X-ray tube by operating the tube at a first voltage while measuring scattered radiation in the first spectral range and then generating the primary beam with the X-ray tube by operating the tube at a second, different voltage while measuring scattered radiation in the second spectral range.

3. Apparatus for measuring an energy-independent X-ray attenuation factor, $A_p$, in a region of an object comprising:

X-ray tube means for generating a primary X-ray beam which traverses the region of the object;

first detector means for measuring radiation which is scattered from a first section of the primary beam which lies in said region of the object;

second detector means for measuring scattered radiation which is scattered from a second section of the primary beam which lies in said region of the object, the first and second detector means being disposed with respect to the object so that radiation from said first and second sections of the primary beam reaches the respective detector means along essentially the same paths through the object;

energy determining means for causing each of the detector means to measure radiation which is scattered from the primary beam in each of a first and a second energy spectral range; and computer means for calculating the attenuation factor from the relationship $$A_p = |d1^*[\ln Q1 - b1] - d2^*[\ln Q2 - b2]|$$

where d1, d2, b1, and b2, are constants, Q1 is the quotient of the values of scattered radiation measured by the first detector means in said two different energy spectral ranges and Q2 is the quotient of the values of scattered radiation measured by the second detector means in each of said energy spectral ranges.

4. The apparatus of claim 3 wherein the energy determining means comprise means for sequentially applying different voltages to X-ray tube means.

5. The apparatus of claim 3 wherein the energy determining means comprise means associated with each of the detector means which causes each detector means to convert measured scattered radiation into two different electrical signals which are respectively representative of radiation in said first and second energy spectral ranges.

* * * * *